United States Patent [19]

McGregor

[11] 4,308,256

[45] Dec. 29, 1981

[54] METHOD OF INDUCING ANALGESIA

[75] Inventor: William H. McGregor, Malvern, Pa.

[73] Assignee: American Home Products Corporation, New York, N.Y.

[21] Appl. No.: 188,641

[22] Filed: Sep. 19, 1980

[51] Int. Cl.$^3$ ............... A61K 31/165; A61K 31/195; A61K 31/235; A61K 37/00
[52] U.S. Cl. .................................. 424/177; 424/308; 424/319; 424/324
[58] Field of Search ............... 424/177, 324, 308, 319

[56] References Cited

PUBLICATIONS

Schnebli et al., Biochimica et Biophysica Acta, 569 (1979 C89–98).

Primary Examiner—Stanley J. Friedman
Attorney, Agent, or Firm—George Tarnowski

[57] ABSTRACT

Bestatin and its analogues are compounds capable of inducing analgesia in mammals when administered peripherally.

1 Claim, No Drawings

METHOD OF INDUCING ANALGESIA

The identification and synthesis of enkephalins in 1975 and the recognition that the amino acid sequence of methionineenkephalin is present in the pituitary prohormone β-lipotropin has been followed by a phenomenal research effort into brain opiates.

Enkephalin, a natural opiate receptor agonist in the brain, has been identified [see Hughes et al., Nature, 258, 577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). It has been suggested that enkephalin receptors may be sites at which morphine-like drugs exert their analgesic activities, and that enkephalins may act as neurotransmitters in brain systems for pain suppression or analgesia. The administration by injection of methionine-enkephalin and leucine-enkephalin into the brain ventricle in rats induces a profound analgesia that is fully reversible by naloxone [see Belluzzi et al., Nature, 260, 625 (1976)].

However, the enkephalins have a number of limitations on their suitability as pharmacological tools. First, natural enkephalins are inactive when administered peripherally, and it is believed that the enkephalins, in general, are rapidly destroyed by blood enzymes. Second, even the endogenously occurring enkephalins are subject to extremely rapid inactivation in brain tissues following their release and action. Such a result would comport with the similar inactivation of many other neurotransmitters.

Research is in progress to elucidate the nature and structure of the enzyme or enzymes responsible for the inactivation of enkephalins. Evidence exists that an aminopeptidase associated with the membranes carrying the opiate receptors with which the enkephalins interact may be implicated in the inactivation of enkephalins. The inactivation proceeds by the very rapid hydrolysis of the enkephalin Tyr-Gly bond, and this cleavage has been extensively studied [see Hambrook et al., Nature, 262, 782–783 (1976); Meek et al., Neuropharmacology, 16, 151–154 (1977); Marks et al., Biochem. Biophys. Res. Commun., 74, 1552–1559; Guyon et al., Biochem. Biophys. Res. Commun., 88, 919–926 (1979)]. It has been further found that an "enkephalinase" is in all probability responsible for the release of the tripeptide Tyr-Gly-Gly from the enkephalins, and that this "enkephalinase" is a dipeptidyl carboxypeptidase [see Malfroy et al., Nature 276, 523–526 (1978); Guyon et al., Life Sciences, 25, 1605–1612 (1979)].

The transient effects of the endogenous enkephalins and the consequent attempts to identify and elucidate the brain enzymes which may be responsible for the inactivation of enkephalins has led to efforts to find compounds which will inhibit the effects of the brain enzymes, thereby potentiating the effects of the enkephalins. For example, antibiotics such as puromycin and bacitracin have been shown to be effective inhibitors of the "aminopeptidase"-catalyzed breakdown of enkephalins [see Knight et al., J. of Biol. Chem., 253, 3843–3847 (1978)], while various naturally-occurring and synthetic peptidic compounds have been shown to inhibit both "aminopeptidase" and "enkephalinase" activity in particulate and soluble fractions from mouse striatum [see Malfroy et al., Nature, 276, 523–526 (1978); Knight et al., J. of Biol. Chem., 253, 3843–3847 (1978); Fournie-Zaluski et al., Biochem. Biophys. Res. Commun., 91, 130–135 (1979)]. However, these data all relate to in vitro experimentation based on mouse brain striata, from which it is not possible to extrapolate the potential in vivo effects of the inhibitors when administered peripherally.

DESCRIPTION OF THE INVENTION

In accordance with the invention, there is now provided a method for inducing analgesia in a mammal in need thereof, which comprises the peripheral administration into said mammal an amount effective to induce analgesia of a compound having the formula:

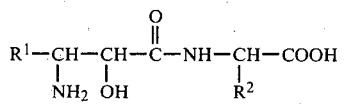

wherein $R^1$ is

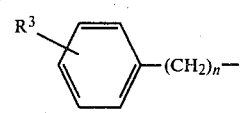

wherein
$R^3$ is hydrogen, chloro, methyl, nitro, hydroxy or amino and n is 0 or 1 and
$R^2$ is lower alkyl of 1 to 6 carbon atoms, hydroxy lower alkyl, alkylthioalkyl, carboxamido-lower alkyl or carboxy lower alkyl provided that when $R^1$ is benzyl and $R^2$ is isobutyl the configuration of the compound is (2S,3R,2'R), (2S,3S,2'S) or (2S,3S,α'R) and the pharmacologically acceptable salts thereof.

It has been found that [(2S,3R)-3-amino-2-hydroxy-4-phenylbutanoyl]-L-leucine (Bestatin) and related compounds, when administered peripherally to a mammalian species, is capable of inducing analgesia in such a mammal. Bestatin and related compounds, which are disclosed and described in U.S. Pat. No. 4,189,604, are known to be inhibitors of aminopeptidase B, leucine aminopeptidase and bleomycin hydrolase, and these compounds enhance the anti-tumor effect of bleomycin and exhibit an antifertility effect.

While no mode of action for bestatin and its related compounds can be advanced with any degree of certitude, it is postulated that bestatin may inhibit one or more of the brain enzymes which may be implicated in the inactivation of the endogenous enkephalins and perhaps even in the inactivation of the endogenous α-, β- and δ-endorphins (of which the N-terminal portion of β-endorphin corresponds to the amino acid sequence of methionine-enkephalin), which are large opiate-like peptides that are thought to breakdown to produce the enkephalins. The most significant aspect of the invention is that bestatin and its related compounds can be administered peripherally to induce analgesia. In the context of the postulated mode of action, then, bestatin and its related compounds can be administered by pharmacologically conventional routes to inhibit the enkephalin-inactivating brain enzyme or enzymes, and thereby potentiate the effects of the endogenous enkephalins and/or endorphins.

The method of preparation of bestatin and its related compounds is described in U.S. Pat. No. 4,189,604.

The pharmaceutically acceptable salts of the compounds used in the invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

In carrying out the method of this invention the active compound can be administered either alone or in combination with inert pharmaceutically acceptable carriers in a variety of dosage forms, orally or parenterally. The dose requirements will vary with the severity of the pain, the animal being treated, the compound employed or the dosage form employed. Thereapy is instituted at low dosages and the dosage is increased incrementally until the desired analgesic effect is achieved.

With large animals (about 70 kg. body weight), by the parenteral route, by intravenous injection, the dose is from about 3 to about 6 mg/kg., and by subcutaneous injection, the dose is from about 9 to about 18 mg/kg. The compounds can also be administered orally.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportions of the active ingredient in a dosage form must be sufficient to impart analgesic activity thereto.

The analgesic activity of bestatin and its related compounds has been demonstrated in rats as described in the following Example:

EXAMPLE 1

The D'Amour-Smith rat tail-flick procedure is an analgesia test with high selectivity for opiate-like activity, tending to yield negative results for other drugs, even non-opiate analgesics. Accordingly, it is the preferred test for enkephalin activity.

Intraventricular cannulae, made of 27-gauge stainless steel tubing, are implanted in 300–400 g. male Charles River rats under pentobarbital anesthesia. After a recovery period of at least one week, the rats are restrained in a wire-mesh cylindrical chamber so that the tip of the tail can be positioned at the focal point of a radiant heat source. After an acclimatistation period of 5 minutes, the lamp is turned on and an electric clock activated. Movement of the tip of the tail exposes a photocell to the lamp, which turns off the thermal stimulus and stops the clock. If a rat fails to move its tail within 8 seconds, the heat is automatically turned off to prevent blistering. The intensity of the lamp is adjusted in each case to produce at least three baseline tail-flick latencies of 2.5–4.5 seconds. Tests are initially made every 2 minutes, then every 5 minutes and finally every 15 minutes.

Initially, using the above outlined procedure, the effects of intraventricularly administered leucine-enkephalin are tested in rats according to the above procedure. The results are summarized in Table 1.

|  | Time (in minutes) - Latency (in seconds) |
|---|---|
| Rat 1: | 2–8.00; 4–8.00; 6–8.00; 8–8.00; 10–6.15; 12–5.76; 14–2.69 |
| Rat 2: | 2–8.00; 4–8.00; 6–5.11; 8–4.24; 10–3.48; 12–4.15 |
| Rat 3: | 2–4.88; 4–8.00; 6–7.50; 8–8.00; 10–4.50; 12–3.49; 14–3.04 |
| Rat 4: | 2–6.47; 4–6.97; 6–6.62; 8–7.17; 10–6.81; 12–7.52; 14–3.06 |

These results show that exogenously administered leucine-enkephalin reaches its peak effect in about 6–8 minutes and that after 10–12 minutes the effect dissipates rapidly.

The rat tail flick procedure is repeated, first by the simultaneous intraventricular injection of both leucine-enkephalin and bestatin and then by the initial injection of bestatin followed one hour later by the injection of leucine-enkephalin. The results of these tests are summarized in Table 2.

TABLE 2

200 µg. of leucine-enkephalin in 10 µl. of modified Ringer's solution and 200 µg. of bestatin in 20 µl. of modified Ringer's solution injected into lateral ventricle of 1 rat.

Time (in minutes)- Latency (in seconds)
2–4.21; 4–5.75; 6–800; 8–8.00; 10–8.00;
12–8.00; 14–8.00
(time interval of testing changed to
5 minutes because of tail blistering)
19–8.00; 24–8.00; 29–8.00; 34–8.00;
39–8.00; 53–8.00; 58–8.00; 63–4.65; 68–8.00;
73–4.95; 78–2.10

400 µg. leucine-enkephalin in 10 µl. of modified Ringer's solution and 200 µg. of bestatin in 10 µl. of modified Ringer's solution injected into lateral ventricle of 1 rat.

Time (in minutes) - Latency (in seconds)
2–7.31; 4–7.56; 6–5.78; 8–6.69; 10–6.99;
12–8.00; 14–8.00; 16–6.50; 18–5.31; 20–2.31;
22–8.00; 24–6.23; 26–8.00; 28–8.00; 30–8.00;
32–4.90; 34–8.00; 36–8.00; 38–4.75; 40–8.00;
42–3.21; 44–3.29; 46–2.47

The above results show that when given simultaneously, bestatin is able to very significantly extend the analgesic effect of leucine-enkephalin.

The above procedure is repeated again, however, the bestatin is administered first and then one hour later the leucine-enkephalin is administered. The results are summarized in Table 3.

TABLE 3

200 µg. of bestatin in 20 µl. of modified Ringer's solution injected into lateral ventricle of 1 rat, and one hour later 200 µg. of leucine-enkephalin in 10 µl. of modified Ringer's solution is likewise injected into the same rat. The results are based on readings taken after the injection of leucine-enkephalin.

Time (in minutes) - Latency (in seconds)
2–8.00; 4–8.00; 6–8.00; 8–8.00; 10–8.00;
12–8.00; 14–8.00; 19–8.00; 24–8.00; 29–8.00;
34–8.00; 53–8.00; 58–8.00; 63–6.07; 68–2.62

The results show that the analgesic effects of leucine-enkephalin can be extended by bestatin even when the latter is administered one hour prior to administration of the leucine-enkephalin.

The effects of bestatin alone are tested in rats according to the rat tail flick procedure. Rats are dosed with 200 µg. and 400 µg. of bestatin and the results are summarized in Table 4.

TABLE 4

200 μg. of bestatin in 10 μl. of modified Ringer's solution is administered into the lateral ventricle of one rat.

Time (in minutes) - Latency (in seconds)

Rat 1: 2-4.92; 4-7.36; 6-4.24; 8-8.00; 10-8.00;
12-8.00; 14-6.41; 16-8.00; 18-8.00; 20-7.39;
22-8.00; 24-8.00; 26-7.09; 28-8.00; 30-8.00;
32-3.56; 34—8.00; 36-3.26; 38-2.64; 40-3.51;
42-4.24; 44-2.81

The results show that at the 200 μg. level, bestatin does not appear to induce any clearcut analgesia.

400 μg. of bestatin in 20 μl. of modified Ringer's solution is administered into the lateral ventricle of two rats.

Time (in minutes) - Latency (in seconds)

Rat 1: 2-4.07; 4-8.00; 6-8.00; 8-8.00; 10-8.00;
12-8.00; 14-8.00; 16-8.00; 18-8.00; 20-8.00;
22-8.00; 24-8.00; 26-8.00; 28-8.00; 30-8.00;
35-8.00; 40-8.00; 45-8.00; 50-8.00; 55-8.00;
60-8.00; 75-8.00; 90-8.00; 105-8.00; 120-8.00;
135-8.00; 150-8.00; 165-8.00; 180-8.00; 195-8.00;
210-8.00; 225-8.00; 240-8.00; 255-4.71

Rat 2: 2-2.16; 4-5.40; 6-4.62; 8-6.51; 10-8.00;
12-8.00; 14-8.00; 16-8.00; 18-8.00; 20-8.00;
22-8.00; 24-8.00; 26-8.00; 28-8.00; 30-8.00;
35-8.00; 40-8.00; 45-8.00; 50-8.00; 55-8.00;
60-8.00; 75-8.00; 90-8.00; 105-8.00; 120-8.00;
135-8.00; 150-8.00; 165-8.00; 180-8.00; 195-8.00;
210-8.00; 225-8.00; 240-8.00; 255-8.00; 270-8.00;
285-8.00; 300-5.19; 315-4.32; 330-4.11

These results show that at the 400 μg. level, bestatin is capable of inducing a very potent analgesia lasting approximately 4½ hours–5 hours whether by preventing the inactivation of endogenous enkephalins and/or endorphins or by some other mode of action.

What is claimed is:

1. A method for inducing analgesia is a mammal in need thereof, which comprises the peripheral administration into said mammal of an amount effective to induce analgesia of a compound having the formula:

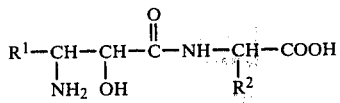

wherein $R^1$ is

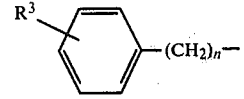

wherein
$R^3$ is hydrogen, chloro, methyl, nitro, hydroxy or amino and n is 0 or 1 and
$R^2$ is lower alkyl of 1 to 6 carbon atoms, hydroxy lower alkyl, alkylthioalkyl, carboxamido-lower alkyl or carboxy lower alkyl, provided that when $R^1$ is benzyl and $R^2$ is isobutyl the configuration of the compound is 2S,3R,2'R), (2S,3S,α'S) or (2S,3S,2'R) and the pharmacologically acceptable salts thereof.

* * * * *